United States Patent
Monteleone et al.

(10) Patent No.: US 7,904,822 B2
(45) Date of Patent: Mar. 8, 2011

(54) SYSTEM AND USER INTERFACE FOR CONFIGURING AND PRESENTING A TREND INDICATIVE DISPLAY OF PATIENT MEDICAL PARAMETERS

(75) Inventors: Rand J. Monteleone, Acton, MA (US); Judith Shaffer, Orchard Park, NY (US); Mark Penny, Salem, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 2307 days.

(21) Appl. No.: 10/410,549

(22) Filed: Apr. 9, 2003

(65) Prior Publication Data

US 2004/0024615 A1 Feb. 5, 2004

Related U.S. Application Data

(60) Provisional application No. 60/374,910, filed on Apr. 23, 2002, provisional application No. 60/374,911, filed on Apr. 23, 2002.

(51) Int. Cl.
*G06F 3/048* (2006.01)
*G06F 17/21* (2006.01)
*G06Q 10/00* (2006.01)
*G06Q 50/00* (2006.01)
(52) U.S. Cl. .............. 715/764; 715/217; 715/212; 705/2
(58) Field of Classification Search ...... 705/2; 715/764, 715/217, 212
See application file for complete search history.

(56) References Cited

U.S. PATENT DOCUMENTS 4,878,175 A * 10/1989 Norden-Paul et al. ............ 705/2
(Continued)

FOREIGN PATENT DOCUMENTS

EP 0 676 709 A2 10/1995

OTHER PUBLICATIONS

Chelewski,Paula K; Designing a patient-care 24-hour flowsheet, Apr. 1998, Nursing Management; Chicago. vol. 29,Iss.4;p. 37.*

*Primary Examiner* — William L Bashore
*Assistant Examiner* — Jordany Núñez
(74) *Attorney, Agent, or Firm* — Jack Schwartz & Associates, PLLC (57) ABSTRACT

A system provides an electronic patient parameter Flowsheet offering the flexible features of a paper chart by enabling user configurability of a Flowsheet trend indicative display to incorporate and locate desired patient parameters and associated data items and properties and to hide non-critical supplementary data. A system configures a user interface presenting patient medical parameter data in a trend indicative display indicating a time period comprising user selectable acquisition time intervals. An acquisition processor acquires, from a patient monitoring device, data representing a patient parameter. A processor initiates generation of data representing at least one display image for use in configuring a trend indicative display of a patient parameter and an associated data item by enabling user selection of the data item for trend indicative display and by enabling user association of the data item with a property indicating at least one of, (a) the data item represents volume data to be used in patient fluid infusion or output calculation, (b) the data item represents a rate for use in calculation of volume of patient fluid infusion or output and (c) the data item value is to be used in multiple acquisition time intervals of the trend indicative display.

3 Claims, 11 Drawing Sheets

U.S. PATENT DOCUMENTS

| | | | |
|---|---|---|---|
| 5,041,086 A | 8/1991 | Koenig et al. | 604/65 |
| 5,208,907 A * | 5/1993 | Shelton et al. | 715/200 |
| 5,247,611 A * | 9/1993 | Norden-Paul et al. | 715/504 |
| 5,438,983 A | 8/1995 | Falcone | 128/630 |
| 5,682,526 A | 10/1997 | Smokoff et al. | 395/615 |
| 5,713,856 A | 2/1998 | Eggers et al. | 604/65 |
| 5,832,448 A * | 11/1998 | Brown | 705/2 |
| 5,946,659 A * | 8/1999 | Lancelot et al. | 705/3 |
| 6,058,326 A | 5/2000 | Hess et al. | 607/9 |
| 6,246,992 B1 * | 6/2001 | Brown | 705/2 |
| 6,416,493 B1 | 7/2002 | Del Giglio | 604/96.01 |
| 2002/0165737 A1 | 11/2002 | Mahran | 705/3 |
| 2003/0036925 A1 | 2/2003 | Miller | 705/2 |

\* cited by examiner

SYSTEM AND USER INTERFACE FOR CONFIGURING AND PRESENTING A TREND INDICATIVE DISPLAY OF PATIENT MEDICAL PARAMETERS

This is a non-provisional application of provisional application Ser. No. 60/374,910 by R. J. Monteleone et al. filed Apr. 23, 2002 and of provisional application Ser. No. 60/374,911 by R. J. Monteleone et al. filed Apr. 23, 2002.

FIELD OF THE INVENTION

This invention is related to the processing and displaying of medical information, and more particularly to processing and displaying patient medical data for user configurable display in a network environment.

BACKGROUND OF THE INVENTION

Patient medical parameter data is acquired, collated, stored and displayed for use in providing patient clinical care in hospitals, clinics, and other healthcare delivery settings. Patient medical parameter data may include vital signs ventilator information, infusion pump data associated with fluid delivery and other data. Such patient medical parameter data is typically displayed on a patient monitoring device screen in a trend indicative chart with a time axis. This type of chart is commonly termed a Flowsheet. A patient monitoring device is usually located at a patient bedside or nursing station in a hospital ward or in an intensive care, surgical or other location and may be connected to a network such as the Internet, a LAN, a WAN or an intra-net for acquiring patient parameter data from local sources (e.g., patient attached sensors) or remote sources (e.g., a remotely stored electronic patient record). The Flowsheet is an electronic chronological chart of patient information that substitutes for a paper vital sign Flowsheet.

It is desirable that an electronic Flowsheet offer similar or better features and flexibility than a paper Flowsheet chart that it replaces. Such paper Flowsheet charts are used by healthcare personnel to record patient Fluid Intake and Output information in many different ways. Known systems provide an electronic Fluids Flowsheet that is limited in its capabilities. Specifically, some known systems restrict flexibility in use of an electronic Flowsheet by employing fixed formats for different types of Fluid intake or output parameter. Other known systems restrict user ability to associate data items to acquired patient parameters and to locate such data items in a desired position within a Flowsheeet. Further, a Flowsheet may become encumbered and cluttered with data items associated with patient parameters thereby impeding its ability to rapidly and accurately convey patient parameter information to a user. These restrictions mean that known systems provide electronic Fluids Flowsheet that fail to replicate the look, features and flexibility of Flowsheet paper charts. A system according to invention principles addresses these limitations and derivative problems.

SUMMARY OF THE INVENTION

A system provides an electronic patient parameter Flowsheet offering increased flexibility by enabling user configurability of a Flowsheet trend indicative display to incorporate and locate desired patient parameters and associated data items and properties and to hide non-critical supplementary data. A system configures a user interface presenting patient medical parameter data in a trend indicative display indicating a time period comprising user selectable acquisition time intervals. An acquisition processor acquires, from a patient monitoring device, data representing a patient parameter. A processor initiates generation of data representing at least one display image for use in configuring a trend indicative display of a patient parameter and an associated data item by enabling user selection of the data item for trend indicative display and by enabling user association of the data item with a property indicating at least one of, (a) the data item represents volume data to be used in patient fluid infusion or output calculation, (b) the data item represents a rate for use in calculation of volume of patient fluid infusion or output and (c) the data item value is to be used in multiple acquisition time intervals of the trend indicative display.

DETAILED DESCRIPTION

Figure 1:
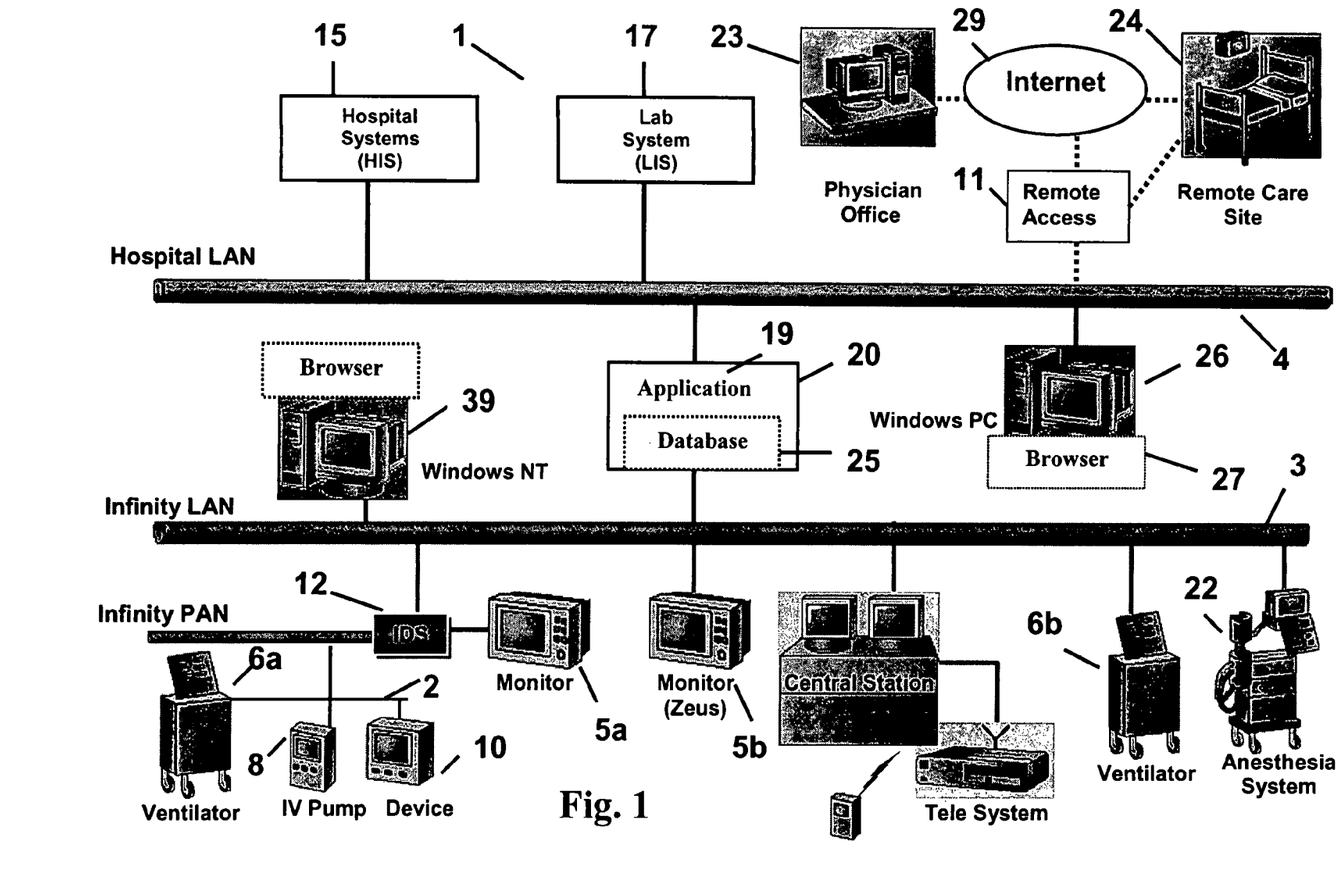
FIG. 1 is a block diagram of a communication network with various devices, according to the principles of the invention.

FIG. 1 is an exemplary block diagram of a communication network incorporating server 20 hosting executable application 19 providing a trend indicative user interface display of patient parameters (termed a Flowsheet) within identified acquisition time intervals. A Flowsheet may contain different types of fluid parameters, including Intra-Venous fluids, drip administered medications, blood products, etc. Such parameters contain different pieces of data that are important to describe a particular fluid. Further, hospitals typically employ different practices concerning the data to be included with each parameter and the manner of displaying this data. A Flowsheet generation and configuration system according to invention principles advantageously enables customization of a Flowsheet to provide increased flexibility by supporting incorporation and location of desired patient parameters and associated data items and properties Further, known Flowsheet systems become encumbered and cluttered with supplementary data items associated with patient parameters (e.g., a Blood Bank number of a particular blood product) thereby impeding the ability of the Flowsheet to rapidly and accurately convey patient parameter information to a user. The inventors have advantageously recognized that this supplementary data may be hidden in the trend indicative display until a user selects a particular label or image element within a Flowsheet trend indicative display.

In an alternative embodiment, the executable application providing the Flowsheet user interface may be resident in another processing device in any part of the network shown in FIG. 1. Communication network 1 (FIG. 1) is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown In FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a patient's room to administer care to a particular patient and to monitor the particular patient. Various medical devices may be connected via MIB 2; examples shown in FIG. 1 comprise a ventilator 6a, IV (Intravenous) Pump 8 or other medical equipment 10. MIB 2 is typically connected to a second level LAN network 3 through an Interface Docking Station (IDS) device 12, for interfacing to Ethernet-compatible LAN network 3. The LAN 3 may be for example, an Infinity LAN, marketed by Siemens Medical System. This higher-level LAN 3 is typically, though not necessarily, used by a particular department within a hospital, such as an intensive care department or surgery department, etc., depending on the size of the organization.

Although not shown in FIG. 1, more than one MIB may be connected to the second level LAN 3, so that more than one patient may be monitored or provided with care through LAN 3. In addition, medical devices may be connected directly to higher-level LAN 3. For example, as shown in FIG. 1, a ventilator 6b and an anesthesia system 22 are connected directly to LAN 3, without use of a MIB. Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 11 which provides remote, secured access from, for example, a remote doctor's office 23 or a remote care site 24, to the various systems and devices on network 1, through for example, Internet 29. Alternatively, a remote site may also access the remote access gateway 19 directly through, for example, a dial-up telephone port, ADSL, or other types of private connection. Remote access gateway 11 may also be part of server 20, to be described below, instead of standing alone, as well know in the art.

According to the principles of the present invention, executable application 19 (or multiple applications in another embodiment) resides on central server 20 on LAN 3 for gathering and processing data from the peripheral medical devices or facilities coupled to LAN 3 or hospital LAN 4, including laboratory results supplied via laboratory system 17 connected through an HL7 interface, for example. Additional medical parameter data including additional laboratory results acquired from any number of medical devices such as those shown in FIG. 1 may be obtained by server 20 using ASTM messaging, for example. The acquired medical parameters associated with a given patient, including laboratory test results, are acquired from the medical devices on network 1 for display and control on monitors 5a, 5b or PCs 26 and 39 or any other display hosting device at any level of the FIG. 1 network. One skilled in the art can readily recognize that server 20 may reside at any level of the hierarchy of network 1, since all the different levels of LANs (e.g., 3, or 4), as well as remote sites in FIG. 1 are interconnected. An example of server 20, is a Prometheus server, marketed by Siemens Medical System. The server may be hosted, for example, by a computer system that is capable of running Microsoft NT operating system.

Application 19 provides a user interface trend indicative display of patient parameters (a Flowsheet) covering a time period comprising user selectable acquisition time intervals. A user selectable acquisition time interval represented by a column in the Flowsheet covers a time period (typically 3 minutes to 4 hours or another user selectable range) in which patient parameters are acquired. Application 19 automatically filters acquired patient parameter data by selecting a patient parameter value for display in a Flowsheet column representing an individual acquisition time interval. Specifically, the selected patient parameter value is incorporated in an Internet compatible (web based) Flowsheet column representing the individual acquisition time interval. Application 19 advantageously enables a user to customize the Flowsheet trend indicative display of an individual patient parameter. Application 19 initiates generation of multiple display images enabling configuration of display of a patient parameter to include additional data items. These additional data items may include a data item usable in a Flowsheet display of multiple different patient parameters.

Figure 2:
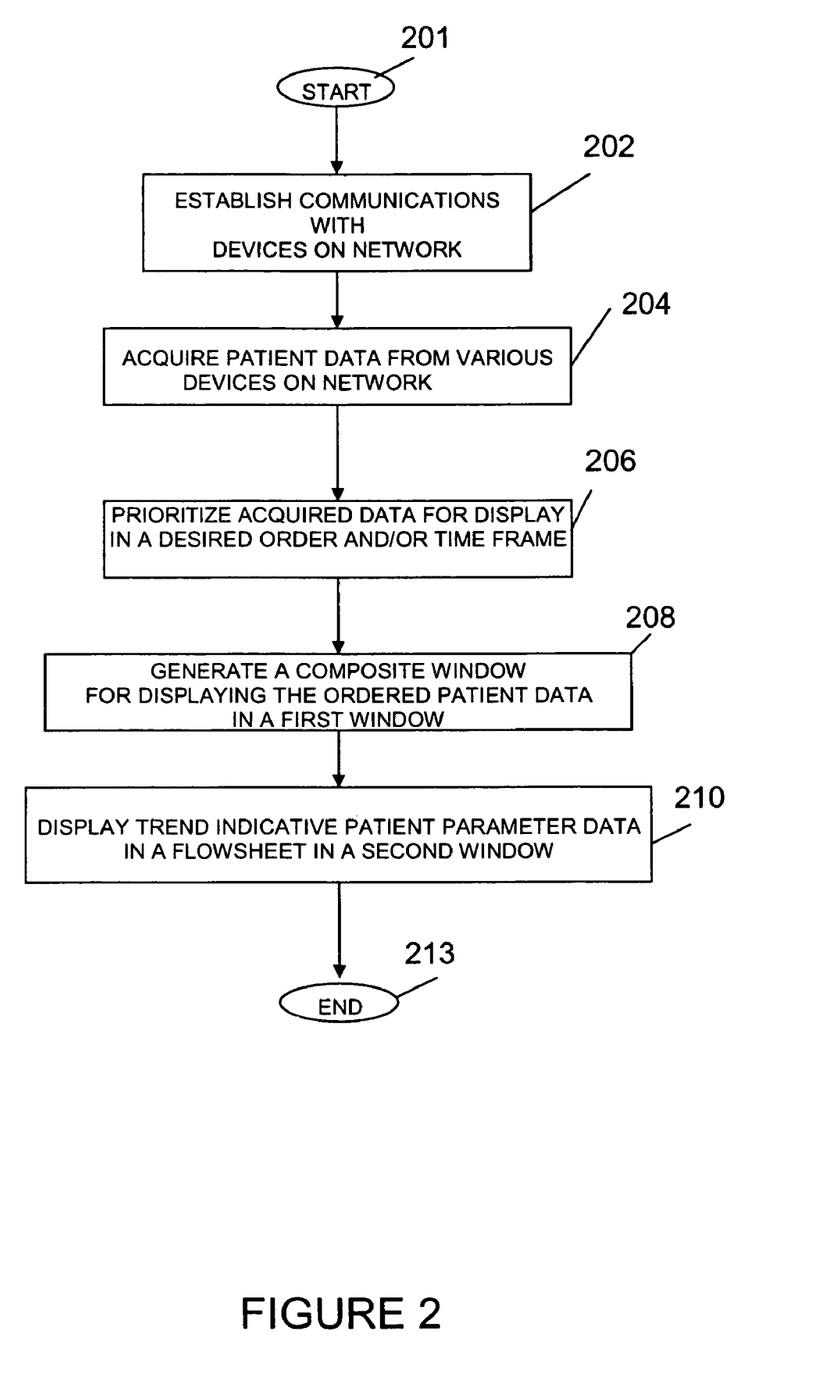
FIG. 2 represents a flowchart of a method for providing a user interface, according to the present invention.

FIG. 2 shows in flow chart form, functions that are performed by executable application 19. Application 19 establishes communication with devices on the network as shown in step 202 after the start at step 201. This is done, for example, by using IP protocol and the known IP device address for each device on the network 1 (FIG. 1), in conjunction with any higher application-layer protocols, as well known in the art. Once communication is established between server 20 and the other devices, application 19, in step 204, starts to acquire parameters that are being monitored, laboratory results and settings selected for the various devices. As previously mentioned, laboratory results may be obtained through an HL7 interface with LIS 17, or via ASTM or MIB point of care (POC) medical devices depicted in FIG. 1.

Medical data and laboratory results may be continuously, periodically or non-periodically acquired and correlated with a given patient for storage in relational data base 25 within server 20. Data base 25 may be of the type used for storing relational data such as the Microsoft SQL server. In addition, application 19 may obtain patient parameter data and patient data comprising medical laboratory results that are first entered and stored, for example, in laboratory system 17 of FIG. 1. Also, application 19 may acquire healthcare provider entered medical notes for display. At step 206, the server 20 application, in response to a user command, prioritizes and stores acquired patient data in server 20, in a desired order and/or time frame for display. Application 19 generates a window for displaying trend indicative patient parameter data including vital signs, ventilator information, infusion pump data associated with fluid delivery and other data in a Flowsheet in steps 208 and 210, for example. The patient parameter data may be a blood pressure parameter, a ventilation parameter, a vital sign parameter, a blood oxygen concentration representative parameter or an infusion pump parameter associated with fluid delivery, for example. Application 19 also generates a composite window for displaying concurrently, for example, a first window showing ordered patient data together with a second window showing patient parameter data, medical laboratory results or user entered medical notes, in steps 208 and 210. The process of FIG. 2 ends at step 213.

In one aspect of the present invention, a user may use a Microsoft Windows compatible PC 26 or Windows NT compatible PC 39 as shown in FIG. 1, or any other processing devices capable of running a menu generating program such as a web browser program (e.g., Microsoft Internet Explorer or Netscape Navigator, etc.) to view a Flowsheet, medical parameters and laboratory results information associated with a given patient. That is, a user may use a web browser on any processing device, as long as a communication connection can be made to server 20 and application 19, to make requests and view information acquired and stored in data base 25. This is advantageous, since a doctor, for example, may gain access to a Flowsheet or laboratory test results from, for example, a remote physician's office 23, without having to access a dedicated terminal. Of course, a user can simply use a keyboard and/or a mouse or any other user interface devices to enter a user selection or request on a user computer, as is known in the art. Application 19 is therefore capable of collating and formatting medical data to be compatible with, for example, HTML (Hypertext Mark-up Language) programming language for displaying data on a web browser. Application 19 is also responsive to, for example, HTTP (Hypertext Transfer Protocol) commands originated from a user's web browser for making a request.

Figure 3:
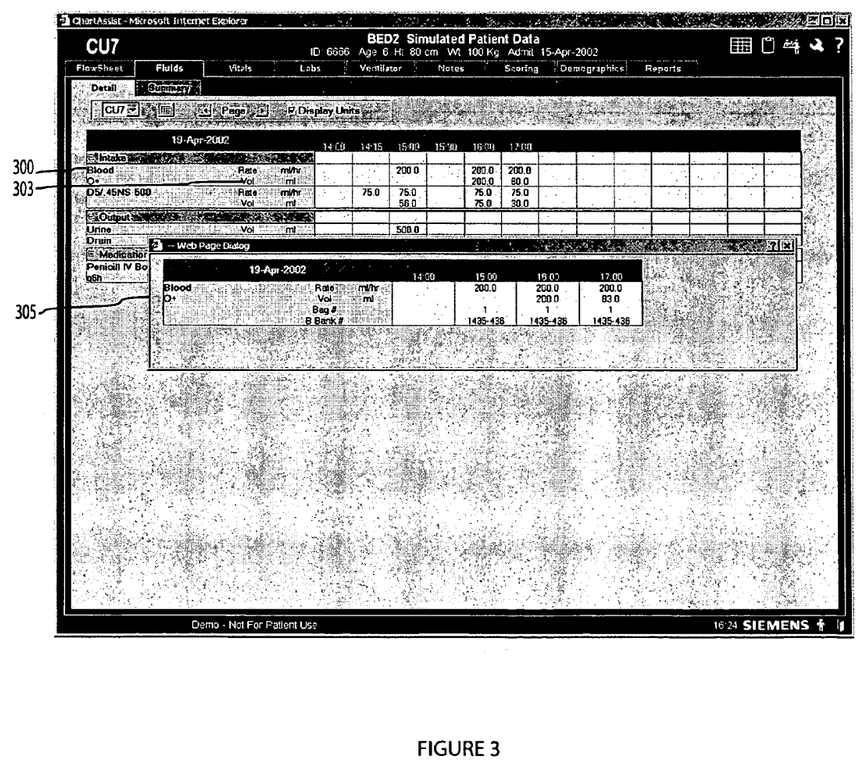
FIG. 3 shows a user interface display image showing patient medical parameter data in a trend indicative display and a popup menu showing supplemental data associated with the patient parameter, according to the present invention.
Figure 10:
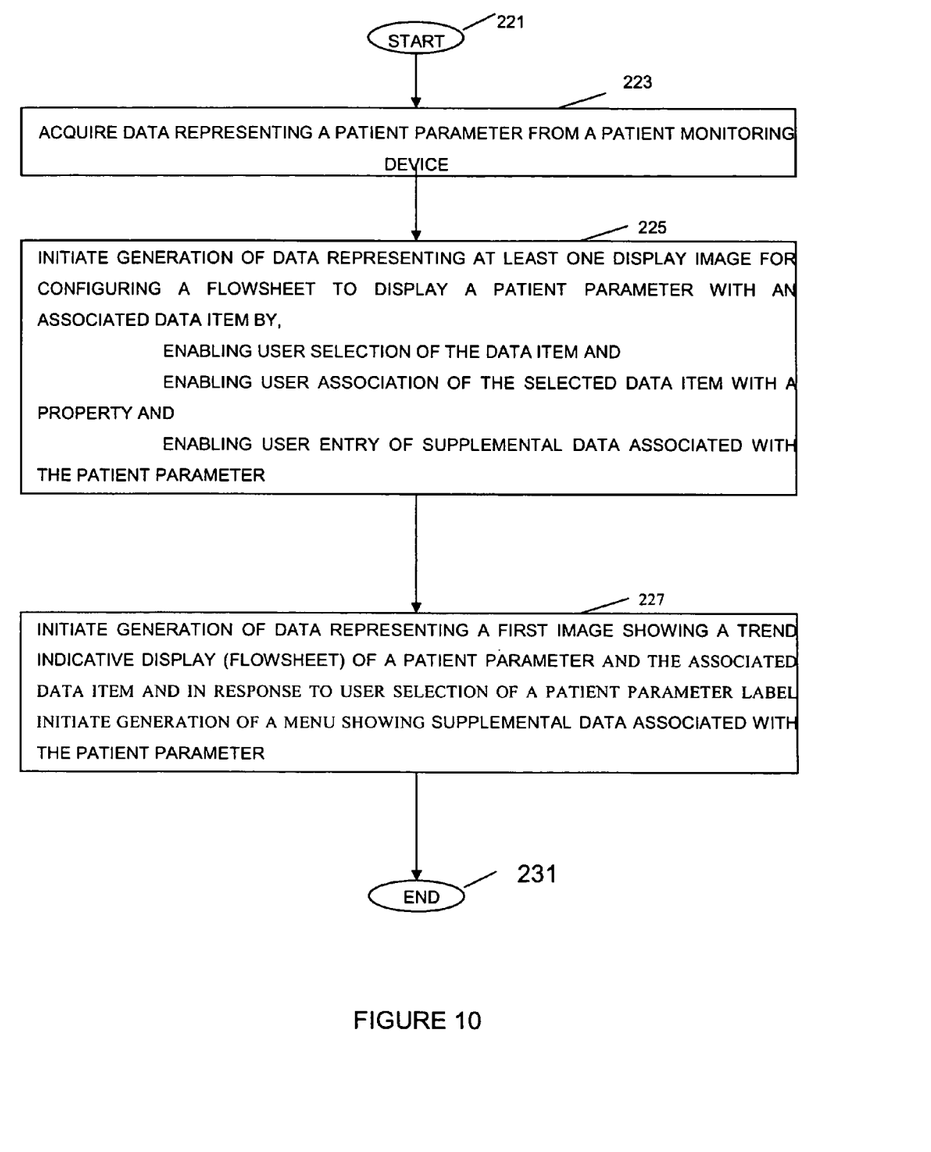
FIG. 10 represents a flowchart of a method for providing display images supporting configuration of a trend indicative display and a resulting configured trend indicative display, according to the present invention.

FIG. 10 represents a flowchart of a method for providing display images supporting configuration of a trend indicative display and for providing a resulting configured trend indicative display. In step 223, following the start at step 221, application 19 acquires data representing a patient parameter from a patient monitoring device in the manner previously described in connection with FIG. 1. Application 19 in step 225 initiates generation of data representing multiple display images for configuring a trend indicative display to show a patient parameter together with an associated data item. A patient parameter comprises, a blood pressure parameter, a ventilation parameter, a vital sign parameter, a blood oxygen concentration representative parameter, a drip medication parameter, an infusion pump parameter associated with fluid delivery or another fluid related parameter, for example. A data item associated with a patient parameter comprises, a volume of patient fluid infusion or output, a rate of volume of patient fluid infusion or output, a blood bank identification number, a blood type identifier, a dosage indicator, an indicator of a drip medication, an intravenous fluid type identifier, a site on a patient associated with said patient parameter or a healthcare worker identifier, for example. FIG. 3 illustrates a trend indicative display showing a patient blood intake parameter 300 in one row of the Flowsheet and an associated blood volume data item 303 in another row of the Flowsheet.

Figure 4:
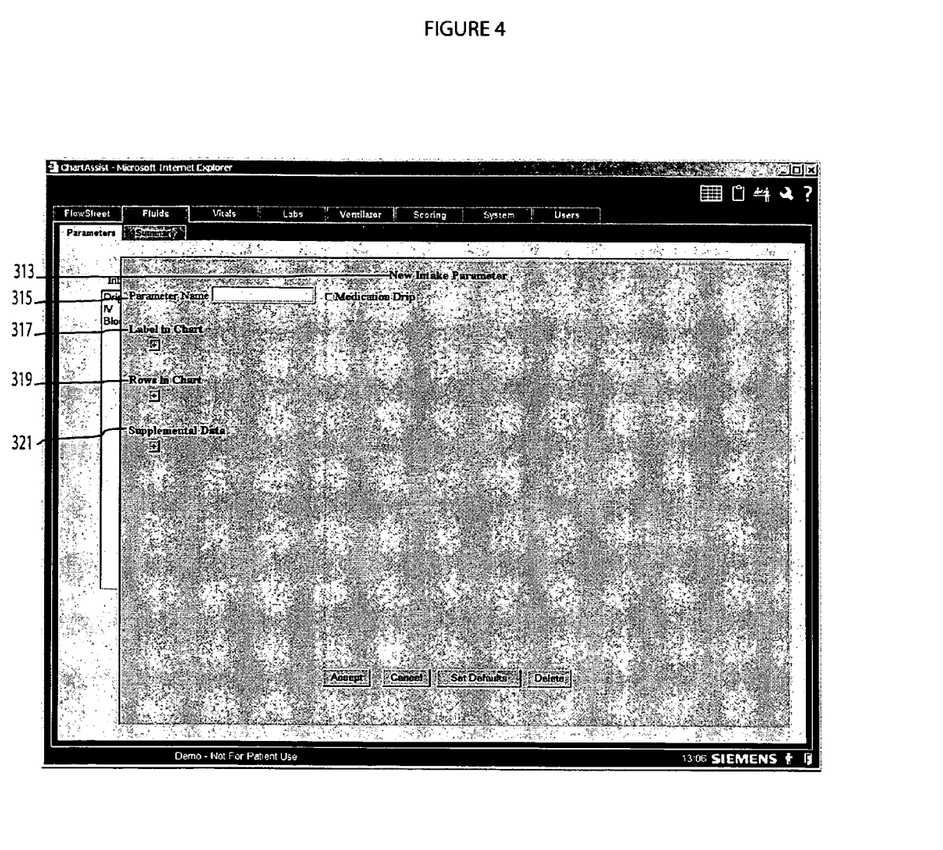
FIGS. 4-9 show user interface display images supporting user configuration of patient parameter data including associated labels, data items, and supplemental data for trend indicative display, according to the present invention.

Application 19 in step 225 initiates generation of data representing multiple display images illustrated in FIGS. 4-9 for configuring a Flowsheet trend indicative display. FIGS. 4-9 show images supporting user configuration of patient parameter data including associated labels, data items, and supplemental data for trend indicative display. FIG. 4 illustrates a new intake patient parameter (313) configuration display image supporting user determination of individual components of a patient parameter identified by user entry of the patient parameter name via item 315. Specifically, the FIG. 4 user interface display image enables a user to initiate selection of components including: a parameter label (via activation of item 317), one or more data items associated with a patient parameter (via activation of item 319) and supplemental data associated with a patient parameter (via activation of item 321). A user determinable parameter label (e.g., item 300 of FIG. 3) is displayed in the leftmost column of the Flowsheet and may occupy one or more character lines. Further, a user is able to select one or more data items (e.g., data item 303) to occupy one or more Flowsheet display rows and also to enter supplemental data associated with a parameter that is advantageously omitted from the trend indicative Flowsheet main display. The supplemental data is viewed in popup menu 305 (FIG. 3) together with Flowsheet data items for a particular parameter in response to user selection of label 300 for the particular parameter, for example, (or in response to user selection of another image element in another embodiment).

Figure 5:
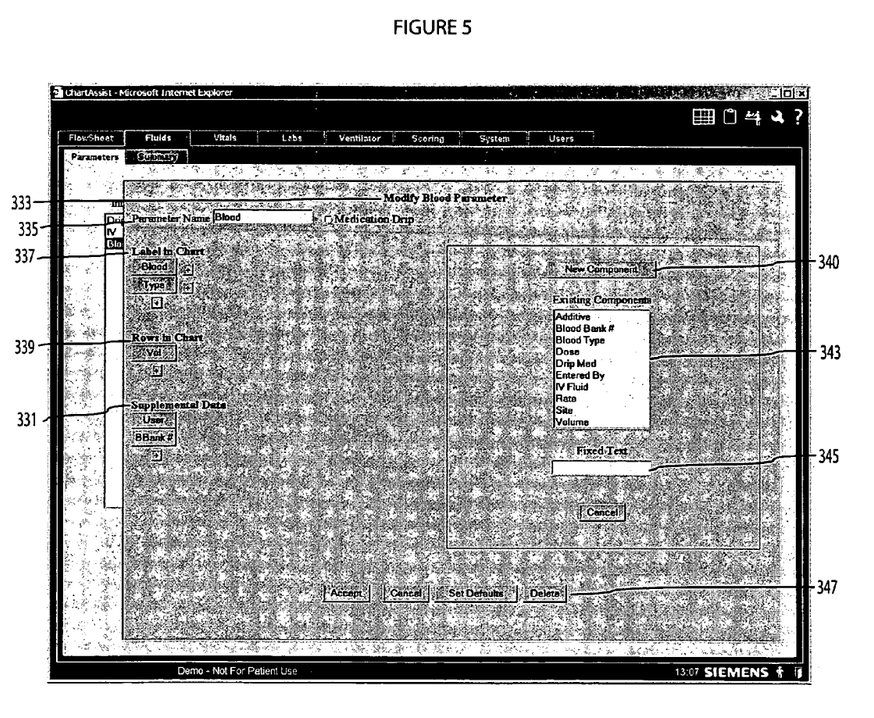
Figure 6:
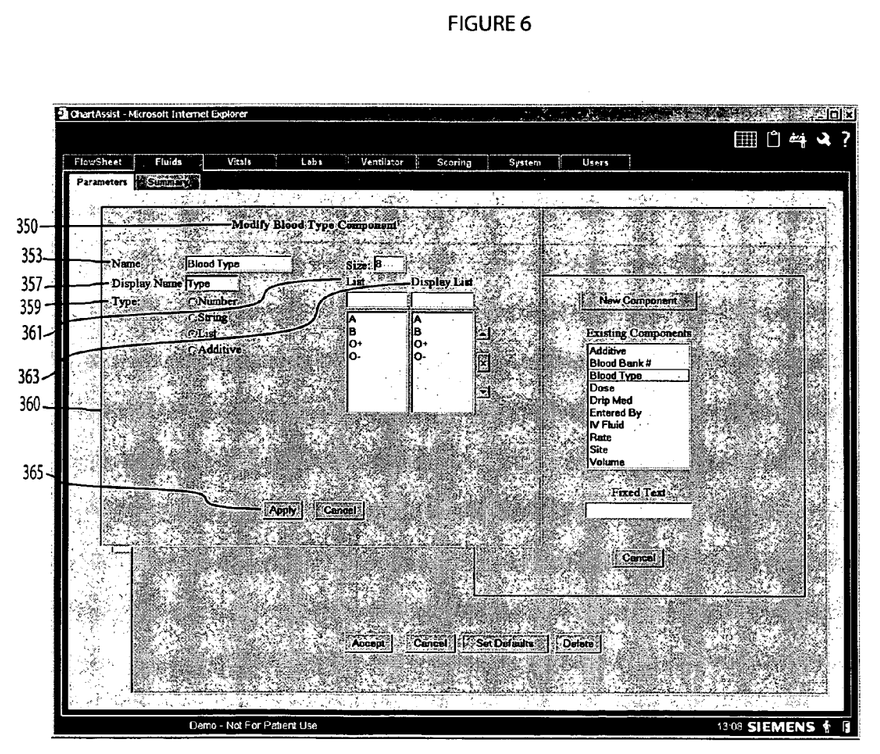
Figure 7:
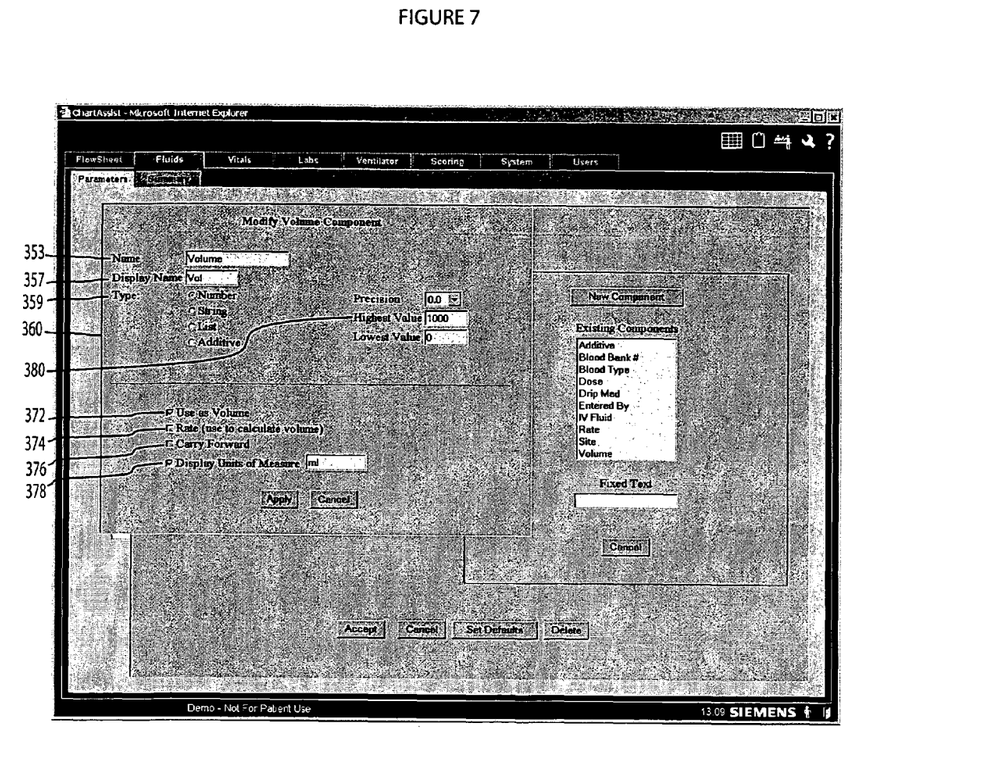

The FIG. 5 user interface image supports user selection of a data item for presentation in a Flowsheet row. The FIG. 5 user interface image is displayed in response to user selection of item 319 in the display image of FIG. 4, for example. The FIG. 5 display image supports modification of a blood parameter (indicated in heading 333) by enabling a user to initiate selection of a data item associated with a patient parameter identified in box 335 (Blood in this example). For this purpose, a user is able to select a data item that has been previously created from a predetermined list of existing data items in menu 343 or may create a new data item via a display image (illustrated in FIG. 6) generated in response to user selection of button 340 (FIG. 5). A user is also able to enter fixed text for display together with a selected or created data item via box 345 and to accept, cancel, delete or set as default data selected via the FIG. 5 user interface image via buttons in menu bar 347. The fixed text may be entered at any position within a parameter label or data item label. For example, a connecting character may be placed between data item labels of a patient parameter or a label may identify a fluid (e.g. Urine) without additional user entered characters or text. FIGS. 5 and 6 and other display images support user selection of text characters to comprise a data item identifier, a parameter label or to be adjacent to a data identifier or a patient parameter label. Items 337 and 339 respectively, indicate labels displayed in the left column of a Flowsheet and data items displayed in rows of the Flowsheet associated with the patient parameter identified in box 335. Item 331 indicates supplemental data associated with the patient parameter of box 335 that is hidden in a Flowsheet but displayed in a pop up menu in response to user selection of a parameter label in the Flowsheet.

A user employs menu window 360 of the FIG. 6 user interface display image to create or modify (as indicated in heading 350) a data item associated with a patient parameter for display in a Flowsheet. The FIG. 6 image illustrates creation of a blood type data item associated with a blood patient parameter. A user enters a name (Blood Type in this example) for a data item via box 353 as well as a corresponding name (Type in this example) in box 357 for display in a Flowsheet. A user further selects a data type via Type options 359 for the data item from options including Number, String, List and Additive (indicating the data item value in a flowsheet patient parameter acquistion time interval is to be summed with other data item values in succeeding acquistion time intervals to produce a cumulative value). Menu window 360 further presents different additional user selectable information associated with corresponding data types depending on the data type selected. For example, for the List data Type 359 option shown selected, menu window 360 presents a user selectable option list 361 enabling a user to select a blood type (from types A, B, O+ and O−) associated with the patient parameter. Menu window 360 presents a similar option list 363 from which a user may select a blood type for inclusion in the Flowsheet trend indicative display. Menu buttons in bar 365 allow a user to accept or cancel configuration data in window 360.

A displayed Flowsheet includes rows of patient parameter data and associated data items presented as one data item per row (as shown in FIG. 3). The user interface display images of FIGS. 6 and 7 advantageously enable a user to select data items and associated properties for a data item row. The FIG. 7 user interface image shows menu window 360 of FIG. 6 used to create a fluid volume data item associated with a blood patient parameter. A user enters a name (Volume in this example) for a data item via box 353 as well as a corresponding name (Vol in this example) in box 357 for display in a Flowsheet. A user selects a Number data type option, for example, via Type options 359. In response, menu window 360 is updated to present user selectable properties 372-378 that may be associated with the user selected data item (Volume in this example). A user may associate the Volume data item with one or more properties including, property 372 indicating a data item is to be used in patient fluid infusion or output calculation, property 374 indicating a data item represents a rate for use in calculation of volume of patient fluid infusion or output, property 376 indicating a data item value is to be used in multiple acquisition time intervals of a trend indicative display and property 378 indicating a unit of measure for a data item. Further, a range and precision for data item values is also determinable by a user via display boxes 380

Figure 8:
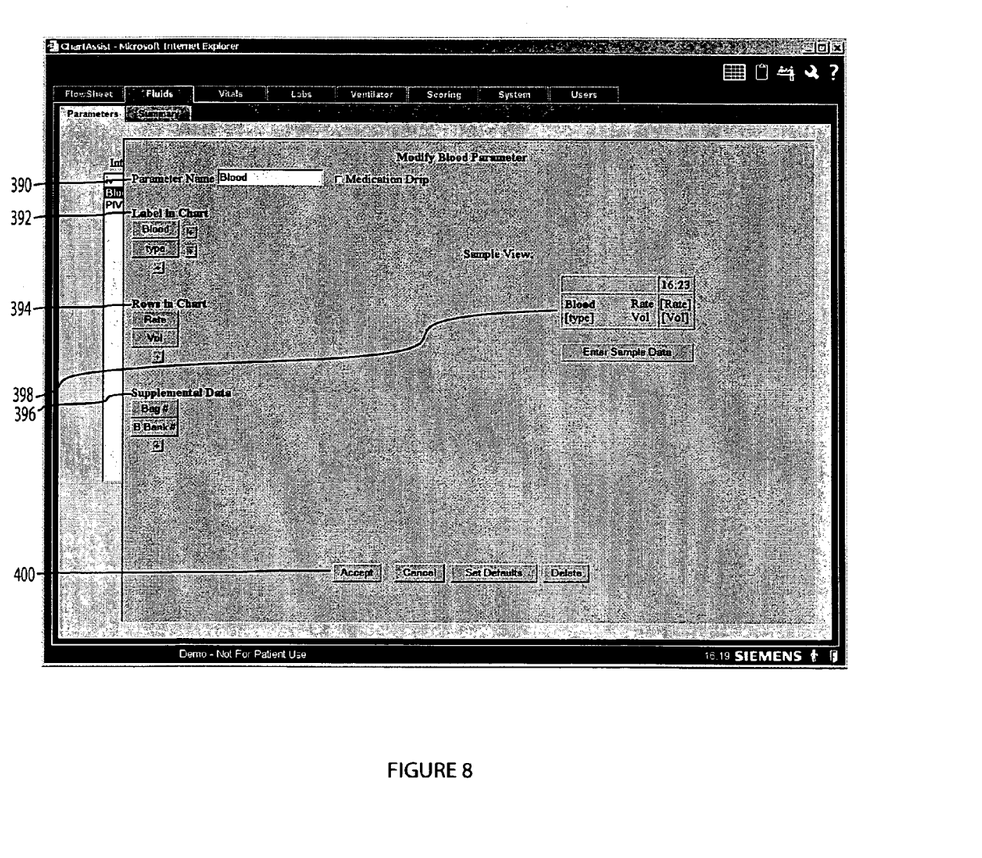

A user is able to select a data item, either to be displayed in a row of a Flowsheet or to be identified as supplemental data that is to be omitted from the Flowsheet and viewed in a popup menu (such as menu 305) in response to user selection of parameter label 300 (FIG. 3), for example. FIG. 8 (in a similar manner to FIG. 5) shows a user interface display image identifying data associated with a patient parameter indicated in box 390. Specifically, FIG. 8 shows labels 392 displayed in the left column of a Flowsheet, data items 394 displayed in rows of the Flowsheet and supplemental data 396 hidden from the Flowsheet but displayed in a pop up menu in response to user selection of a parameter label in the Flowsheet. Parameter label 392 and data items 394 are presented in preview 398 indicating the manner in which these items are to be displayed in a Flowsheet. This faciltates user creation of a desired Flowsheet format. Further, a user is able to accept, cancel, delete or set as default, data selected via the FIG. 8 user interface image via buttons in menu bar 400.

Figure 9:
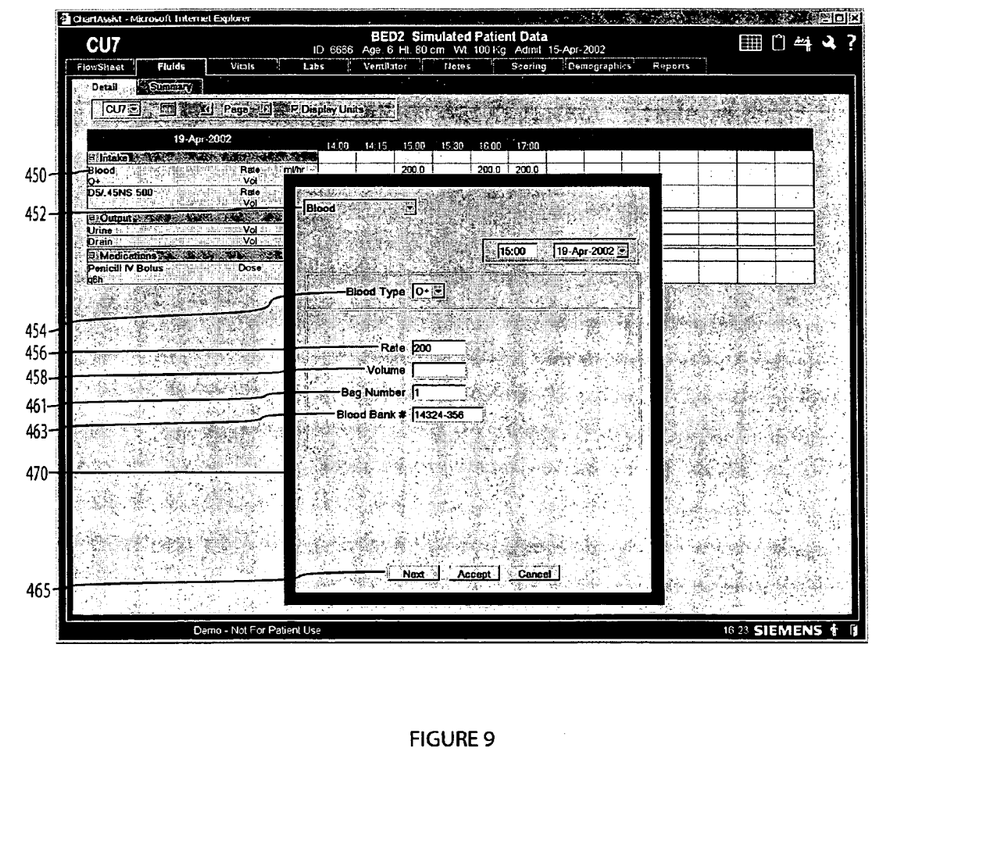

FIG. 9 shows a popup menu 470 indicating user entered data associated with patient parameter 450 in a Flowsheet. Popup menu 470 is presented following user configuration of a Flowsheet to display patient parameter 450 (such as a fluid intake or output parameter) using user interface images as shown in FIGS. 4-8 and in response to user selection of a cell within the displayed Flowsheet. Popup menu 470 contains fields 452 and 454 identifying user entered patient parameter labels (Blood and Blood Type O+ in this example), fields 456 and 458 identifying user entered data items in the Flowsheet, and fields 461 and 463 identifying user entered supplemental data hidden in the Flowsheet but displayable in a pop up menu in response to user selection of a parameter label. Popup menu 470 enables a user to view and modify the data in these fields with the exception of labels 452 and 454 which are modifiable in user interface display images of FIGS. 5 and 6, for example.

Returning to the flowchart of FIG. 10, application 19 in step 227, initiates generation of image data representing a configured Flowsheet trend indicative display of a patient parameter acquired in step 223. Specifically, application 19 generates data representing a trend indicative display illustrated in FIG. 3 showing a patient blood intake parameter 300 in one row and an associated blood volume data item 303 in another row. Further, application 19 in step 227, initiates generation of image data representing supplemental data associated with patient parameter 300 in popup menu 305 together with Flowsheet data items of parameter 300 in response to user selection of label 300 for the particular parameter. The process of FIG. 10 ends at step 231.

Figure 11:
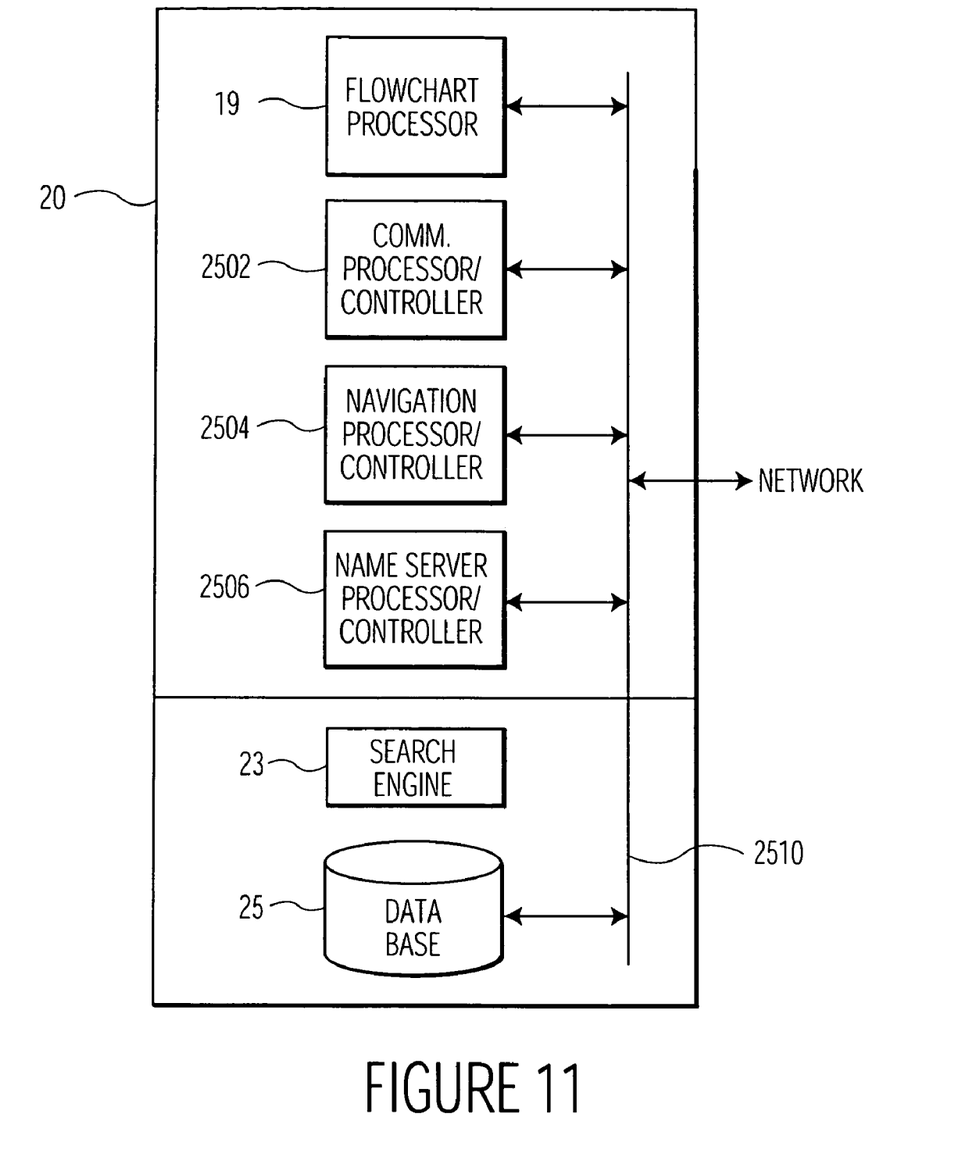
FIG. 11 is a block diagram of a server having functionality in accordance with the present invention.

FIG. 11 shows a block diagram of an exemplary embodiment of server 20 (FIG. 1) including functions in accordance with the present invention for generating data for configuring and presenting a Flowsheet trend indicative display and for managing, collating, searching and updating data base 25 containing patient medical information. Executable applications or processors operative to carry out instructions for performing the various functions described herein include an executable application 19 for performing Flowchart related processing and communications processing module 2502 that acquires the patient data including the monitored parameters allocated to a given patient from the network and collates the information for storage in data base 25. Navigation collation processor 2504 operates in conjunction with the web browser and display generator software to collate and prioritize parameters for display to the user while navigating through various applications selected by a user through the user interface. Name server processor 2506 associates unique identifiers (IDs) with each node connected to the system network and with each patient in the system in order to track and update patient information throughout the system. Input/output data and control signals are used to communicate between the various processors as well as to interface with the data base 25 and search engine 23 and with the network via communication line 2510.

The Flowchart user interface display images, systems and processes presented in FIGS. 1-11 are not exclusive. Other Flowchart configuration and presentation display images, systems and processes may be derived in accordance with the principles of the invention to accomplish the same objectives. Although this invention has been described with reference to particular embodiments, it is to be understood that the embodiments and variations shown and described herein are for illustration only and that various modifications may be implemented by those skilled in the art without departing from the scope of the invention. Flowchart user interface functions supporting flexible, user friendly, Flowchart configuration and presentation formats may be used in any application where different users desire data to be displayed in corresponding different ways. The system advantageously enables a user to create a parameter label from user defined elements and to specify a data item associated with a patient parameter as the rate or volume of the parameter. Further, the system enables supplemental data to be advantageously hidden from particular images to reduce clutter and to be displayed in response to user command.

What is claimed is:

1. A user interface system presenting patient medical parameter fluid data in a trend indicative display indicating a time period comprising patient parameter acquisition time intervals, comprising:

an acquisition processor for acquiring, from a patient monitoring device, data representing a patient parameter;

a processor for initiating generation of data representing at least one display image for configuring a trend indicative display of a patient fluid parameter together with an associated data item, enabling user selection of said data item for trend indicative display and by enabling user association of said selected data item with a first property indicating (a) volume data to be used in patient fluid infusion or output calculation, and a second property indicating (b) a rate for use in calculation of volume of patient fluid infusion or output;

wherein said at least one display image supports association of said patient parameter with (a) a parameter label and (b) supplemental data; and wherein said supplemental data is for display in an image window in response to user selection of an image element in said trend indicative display.

2. A user interface system providing a trend indicative display of patient medical parameter fluid data showing patient parameter acquisition time intervals, comprising:

an acquisition processor acquiring, from a patient monitoring device, data representing a patient parameter; and a processor initiating, in response to user command, generation of data representing at least one display image comprising a trend indicative display of, said patient fluid parameter, and a data item associated with said patient fluid parameter, and with a property indicating at least one of, (a) said data item represents volume data to be used in patient fluid infusion or output calculation and (b) said data item represents a rate for use in calculation of volume of patient fluid infusion or output;

wherein said trend indicative display includes at least one of, (a) a name for said data item, (b) a unit of measure of said data item, (c) a parameter label, (d) an identifier for said data item; and wherein in response to user selection of an image element in said trend indicative display said processor initiates generation of data representing at least one display image including supplemental data associated with said patient parameter.

3. A user interface system according to claim 2, wherein said image element comprises said parameter label.

* * * * *

UNITED STATES PATENT AND TRADEMARK OFFICE
Certificate

Patent No. 7,904,822 B2                                                                                                         Patented: March 8, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Rand J. Monteleone, Acton, MA (US); Judith Shaffer, Orchard Park, NY (US); Mark Penny, Salem, MA (US); and Amy M. Manetta, North Billerica, MA (US).

Signed and Sealed this Seventh Day of October 2014.

*VINCENT N. TRANS*
*Supervisory Patent Examiner*
*Art Unit 2100*
*Technology Center 2100*